United States Patent
Heckel et al.

(10) Patent No.: US 6,675,039 B2
(45) Date of Patent: Jan. 6, 2004

(54) COMPUTED TOMOGRAPHY SCAN PROTOCOL

(75) Inventors: Beth Ann Heckel, Sturtevant, WI (US); David Charles Mack, Waukesha, WI (US); Toan T. Le, Germantown, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/945,281

(22) Filed: Aug. 31, 2001

(65) Prior Publication Data

US 2003/0045792 A1 Mar. 6, 2003

(51) Int. Cl.⁷ .............................................. A61B 5/055
(52) U.S. Cl. ........................ 600/425; 600/300; 345/156
(58) Field of Search ................................. 600/425, 300; 382/128; 345/156

(56) References Cited

U.S. PATENT DOCUMENTS

| | | | |
|---|---|---|---|
| 4,642,621 A | * | 2/1987 | Nemoto et al. ............ 345/634 |
| 4,839,807 A | | 6/1989 | Doi et al. |
| 4,845,480 A | * | 7/1989 | Satou .......................... 345/2.2 |
| 4,945,476 A | | 7/1990 | Bodick et al. |
| 5,660,176 A | | 8/1997 | Iliff |
| 5,807,256 A | | 9/1998 | Taguchi et al. |
| 5,910,107 A | | 6/1999 | Iliff |
| 6,032,678 A | * | 3/2000 | Rottem ....................... 600/437 |
| 6,113,540 A | | 9/2000 | Iliff |
| 6,128,002 A | * | 10/2000 | Leiper ......................... 345/156 |
| 6,206,829 B1 | | 3/2001 | Iliff |
| 6,370,413 B1 | * | 4/2002 | Alvarez et al. ............. 600/407 |

* cited by examiner

Primary Examiner—George Manuel
Assistant Examiner—Barry Pass
(74) Attorney, Agent, or Firm—Carl B. Horton, Esq.; Armstrong Teasdale LLP

(57) ABSTRACT

A review and analyze protocol is described. The protocol comprises the steps of performing a patient scan to collect scan data to be used in generating an image, performing at least one of a single exam review and a dual exam review of images generated using the scan data, and analyzing an area of interest identified in performing the exam review.

18 Claims, 2 Drawing Sheets

COMPUTED TOMOGRAPHY SCAN PROTOCOL

BACKGROUND OF THE INVENTION

This invention relates generally to medical imaging, and more particularly, to a protocol for reviewing and analyzing anatomical areas of interest.

As used herein, the term "protocol" refers to method steps performed in completing a task, such as reviewing and analyzing anatomical areas of interest. The term "lung screening" protocol refers to a method for detection and management of lung tumor growth. A lung screening protocol typically includes, for example, generating images of a lung and then reviewing the images to identify nodules.

In performing a review of images generated by computed tomography (CT), a physician can follow one of many protocols. The specific protocol followed by a particular physician may not necessarily be the fastest review protocol as compared to other protocols, and may not necessarily be the most efficient protocol as compared to other protocols. Rather, the particular physician may simply follow a protocol most familiar to the physician.

BRIEF SUMMARY OF THE INVENTION

In one aspect, a review and analyze protocol is provided. The protocol comprises the steps of performing a patient scan to collect scan data to be used in generating an image, performing at least one of a single exam review and a dual exam review of images generated using the scan data, and analyzing an area of interest identified in performing the exam review.

In another aspect, a method for examining a lung nodule is provided. The method comprises the steps of performing a scan to collect scan data of the nodule, performing at least one of a single exam review and a dual exam review of images of the nodule generated using the scan data, and analyzing the nodule after reviewing the nodule images.

In yet another aspect, a computer program for controlling operation of a computer workstation during a nodule exam and review is provided. The computer program is configured to control a processor to prompt an operator to enter patient history data into the station, prompt an operator to select whether to perform at least one of a single exam review and a dual exam review, and initiate an analyze mode.

DETAILED DESCRIPTION OF THE INVENTION

Although the protocol described below is sometimes described with specific reference to lung screening, it is contemplated that the protocol, or at least some aspects of the protocol, can be utilized in other applications. Of course, the particular analysis and imaging performed can vary from application to application. Therefore, the specific references to lung screening are by way of example only and do not limit use of the protocol to lung screening.

In addition, the protocol is described below in the context of computed tomography (CT). It is believed that the protocol, however, can be practiced in connection with other imaging systems such as ultrasound and magnetic resonance imaging systems.

Further, an example CT system is described below. The protocol can be practiced in connection with a CT system such as the LightSpeed imaging system, which is commercially available from the GE Medical Systems business of General Electric Company, Milwaukee, Wis. The protocol can, however, be used in connection with other CT systems and is not limited to practice with any one particular CT system.

Figure 1:
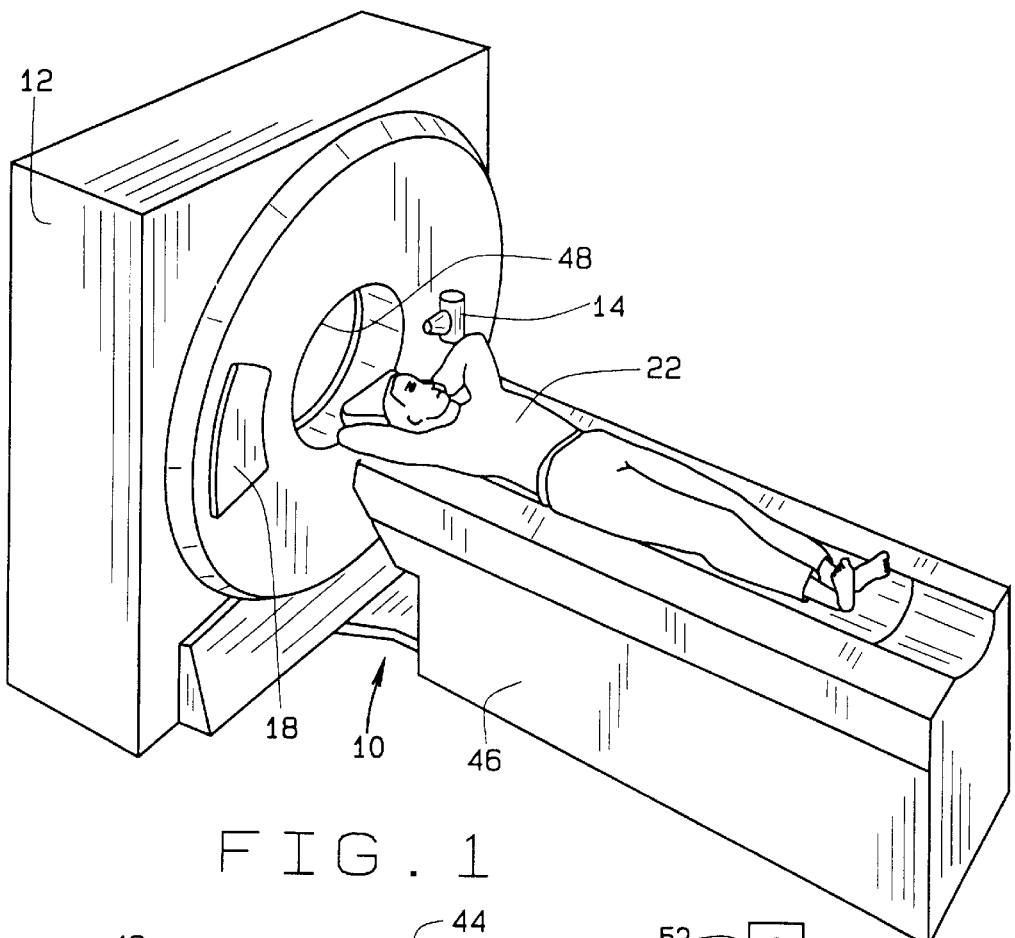
FIG. 1 is a pictorial view of a CT imaging system.
Figure 2:
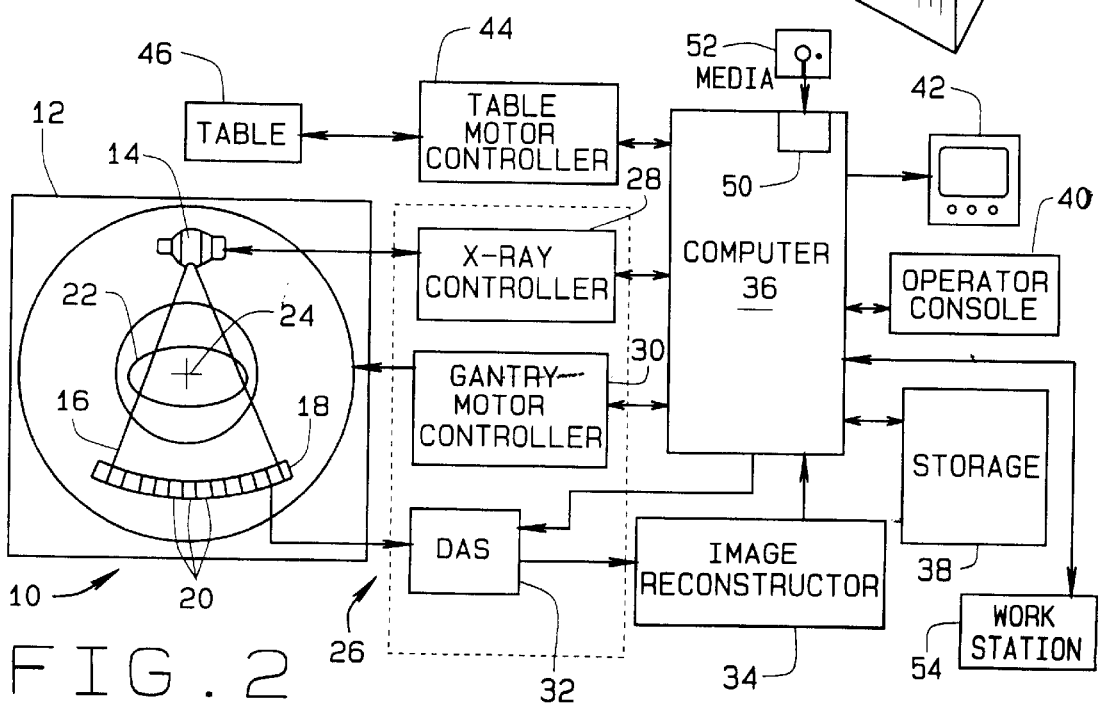
FIG. 2 is a block schematic diagram of the system illustrated in FIG. 1.

Referring to FIGS. 1 and 2, a CT system 10 is shown as including a gantry 12 representative of a "third generation" CT scanner. Gantry 12 has an x-ray radiation source 14 that projects a beam of x-ray radiation 16 toward a detector array 18 on the opposite side of gantry 12. Detector array 18 is formed by detector elements 20 that together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. In one embodiment, detector array 18 is fabricated in a multi-slice configuration. In a multi-slice configuration, detector array 18 has a plurality of rows of detector elements or cells 20, only one of which is shown in FIG. 2. One or more additional rows of detector elements 20 in such configurations are arranged parallel to the illustrated row, and each row is transverse to the translation direction of patient 22 (i.e., the z-axis or patient axis).

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements or cells 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In a helical scan as performed in one embodiments of the present invention, table 46 moves while projection data is being collected and gantry 12 is rotating. The "helical pitch" is a measure of the amount of movement of table 46 per rotation of gantry 12.

In one embodiment, computer 36 includes a device 50 for reading and writing onto removable media 52. For example, device 50 is a floppy disk drive, a CD-R/W drive, or a magneto-optical drive (MOD). Correspondingly, media 52 is either a floppy disk, a compact disk, or a MOD. Device 50 and media 52 are used in one embodiment to transfer acquired projection data from imaging system 10 to another computer (e.g., a post processing workstation) for further processing, or in another embodiment to input machine readable instructions that are processed by computer 36.

In one embodiment, a post processing workstation 54 is coupled to computer 36 and utilized as described below. Workstation 54 includes, for example, a separate computer or processor, or a process sharing one or more CPUs (central processing units) in computer 36. In one embodiment, computer 36 is configured as required to perform a paging review utilizing display 42. Workstation 54 communicates with computer 36 so that data from a CT scan of patient 22 is provided to workstation 54. Also, workstation 54 communicates window/level settings to computer 36 so that a desired image is displayed on display 42. Workstation 54 can also be provided with a separate display unit (not shown) on which images are displayed.

In another embodiment, a computer system separate from imaging system 10 (for example, a workstation, not shown in the figures) is provided. Acquired data and/or reconstructed images are transferred from imaging system 10 to the separate computer system via a network (not shown) or suitable media 52.

Figure 3:
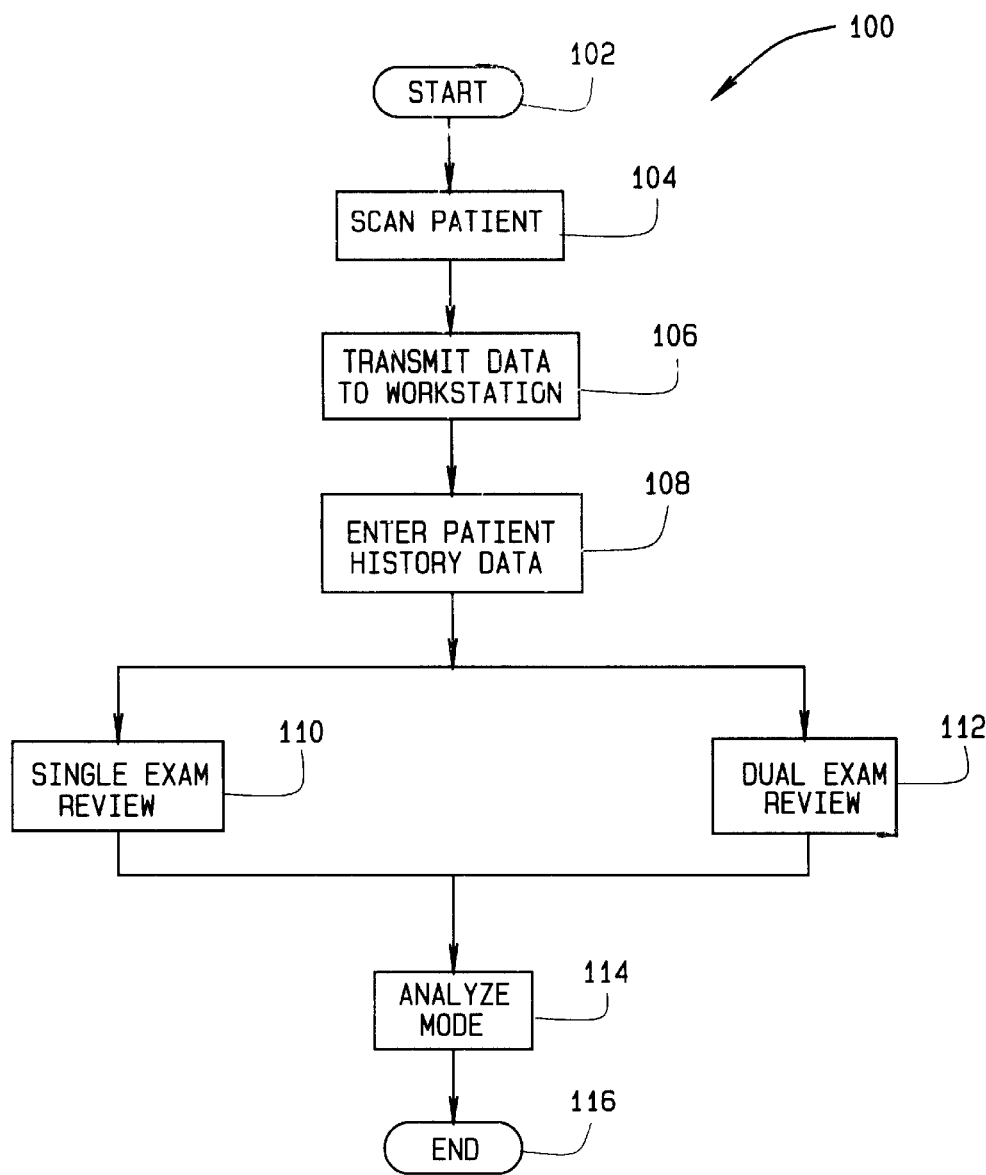
FIG. 3 is a simplified flow chart representative of one embodiment of the present invention.

FIG. 3 is a simplified flow chart 100 of an example protocol. Specifically, after starting 102 execution of the protocol, a patient scan 104 is performed. In the example embodiment, the scan is performed using CT system 10. The specific type of scan performed depends on the region of interest. For example, if the region of interest is a lung, then the lung region can be scanned in a low dose mode, as is known in the art.

Once the scan is complete, the scan data is transmitted 106 to a workstation, e.g., workstation 54. In the example embodiment, the scan data transferred is in the form of image data. Of course, and depending on the workstation configuration and processing capacity, the scan data could be in the form of raw data collected from the scan, projection data, image data, or a combination of all or some of the different types of data. The data is transmitted to workstation via external media (e.g., a compact disc) or via a local or wide area network.

Patient history data also is entered 108 into workstation. Patient history data includes, for example, patient information such as smoking habits, cholesterol levels, and risk factors. The patient history data also can include family history data, such as family history of disease.

After transmitting data to the workstation and entering patient data into the workstation, then an exam review is performed. The exam review can be performed in a single exam review mode 110 or a dual exam review mode 112. In the single exam review mode, one exam is reviewed with multiple viewports. Manual synchronization of the viewports is performed. The operator can page through the images with the same or multiple windows/levels. For example, one set of images can be viewed with a lung window/level and another set of images can be viewed using a soft tissue window/level.

In the dual exam review mode, two or more exams (i.e., data from different scans) can be viewed simultaneously with the same manual synchronization tools as described above in the single exam review mode. In addition to bookmarking slices of interest, bookmarks, regions of interest, and annotation from previously viewed studies is saved on the images so that the operator has a roadmap as to where the areas of interest are located. Linking of nodules between old and new studies also can be performed in the dual exam review mode.

Upon completing the exam review, then an analyze mode 114 is initiated. In the analyze mode, the area of interest can be further analyzed. For example, in a lung scan, a nodule can be further analyzed. Example software tools that can be utilized in such analysis include a shutter tool that encompasses the nodule or other area of interest. Multiple axial view slicing can be used in connection with the shutter tool so that axial slices of the nodule above and below the bookmarked slice of interest can be viewed.

In addition, an image verification tool can be utilized. The image verification tool outlines the area of interest, e.g., a nodule, according to a selected threshold. Characteristics of the area of interest also can be assessed. For a nodule, for example, the nodule size, spiculation, smoothness, and extents can be visually assessed by an operator. It is contemplated that such assessment, or portions of the assessment, can be performed automatically by computer.

The protocol ends 116 upon exiting the analyze mode. The analyze mode can be exited manually by the operator simply selecting exit, or the program can automatically exit upon the occurrence of a predetermined event, e.g., upon completion of a predefined analysis sequence or passage of a predetermined period of time. The images displayed and data are stored in the workstation memory or imaging system memory, for example.

The protocol, or portions of the protocol, can be performed under the control of a computer. For example, in one embodiment, a workstation computer processor is programmed to prompt an operator to enter patient data into the workstation once the scan data has been transferred to the workstation. More specifically, a programmed stored in the workstation memory controls execution of a workstation computer processor to prompt the operator to perform a number of steps or make selections. For example, the processor is programmed to prompt an operator to select whether to perform at least one of a single exam review and a dual exam review, and to initiate the analyze mode.

While the invention has been described in terms of various specific embodiments, those skilled in the art will recognize that the invention can be practiced with modification within the spirit and scope of the claims.

What is claimed is:

1. A review and analyze protocol, comprising:
    performing a patient scan to collect scan data to be used in generating images,
    performing at least one of a single exam review and a dual exam review of the images with multiple viewports,
    bookmarking at least one slice of interest; and
    analyzing an area of interest identified in performing the exam review, wherein analyzing the area of interest includes:
        generating additional slices above and below the bookmarked slice, the additional and the bookmarked slices encompassing the area of interest.

2. A protocol according to claim 1 wherein the patient scan comprises a computed tomography scan.

3. A protocol according to claim 1 further comprising the step of transmitting the scan data to a workstation, and entering patient history data into the workstation.

4. A protocol according to claim 1 wherein the single exam review comprises reviewing images generated using data collected in one exam.

5. A protocol according to claim 1 wherein the dual exam review comprises reviewing a plurality of images, at least one image generated using data collected in a first exam and at least one image generated using data collected in a second exam.

6. A protocol according to claim 1 wherein analyzing the area of interest comprises at least one of:
utilizing a shutter tool to encompass an area of interest,
performing an image verification, and
assessing characteristics of an area of interest.

7. A protocol according to claim 6 wherein the area of interest in a nodule, and wherein assessing characteristics of the area of interest comprises characterizing at least one of nodule size, spiculation, smoothness, and extents.

8. A method for examining a lung nodule, comprising:
performing a scan to collect scan data of the nodule,
generating images of the nodule from the scan data,
performing at least one of a single exam review and a dual exam review of the images with multiple viewports,
bookmarking at least one slice of interest; and
analyzing the nodule after reviewing the nodule images, wherein analyzing the nodule includes:
generating additional slices above and below the bookmarked slice, the bookmarked and the additional slices encompassing the nodule.

9. A method according to claim 8 wherein performing a scan comprises performing a computed tomography scan.

10. A method according to claim 8 wherein prior to performing at least one of a single exam review and a dual exam review, said method comprises the steps of transmitting the scan data to a workstation, and entering patient history data into the workstation.

11. A method according to claim 8 wherein the single exam review comprises reviewing images generated using data collected in one exam.

12. A method according to claim 8 wherein the dual exam review comprises reviewing a plurality of images, at least one image generated using data collected in a first exam and at least one image generated using data collected in a second exam.

13. A method according to claim 8 wherein analyzing the nodule comprises at least one of:
utilizing a shutter tool to encompass an area of interest,
performing an image verification, and
assessing characteristics of an area of interest.

14. A method according to claim 13 wherein assessing characteristics of the nodule comprises characterizing at least one of nodule size, spiculation, smoothness, and extents.

15. A computer readable medium encoded with a program configured to instruct a computer to:
prompt an operator to enter patient history data into a workstation;
prompt the operator to select whether to perform at least one of a single exam review and a dual exam review of images;
prompt the operator to bookmark at least one slice of interest; and
initiate an analyze mode, wherein the analyze mode includes:
generating additional slices above and below the bookmarked slice, the bookmarked and the additional slices encompassing an area of interest.

16. A computer readable medium according to claim 15 wherein the single exam review comprises reviewing images generated using data collected in one exam, and the dual exam review comprises reviewing a plurality of images, at least one image generated using data collected in a first exam and at least one image generated using data collected in a second exam.

17. A computer readable medium according to claim 15 wherein the analyze mode comprises at least one of:
utilizing a shutter tool to encompass an area of interest,
performing an image verification, and
assessing characteristics of an area of interest.

18. A computer readable medium according to claim 17 wherein assessing characteristics of the nodule comprises characterizing at least one of nodule size, spiculation, smoothness, and extents.

* * * * *